US005756106A

United States Patent [19]
Concannon et al.

[11] Patent Number: 5,756,106
[45] Date of Patent: May 26, 1998

[54] DISCRETE HAIR CARE COMPOSITION

[75] Inventors: Linda M. Concannon, Nutley; Joseph C. Hourihan, Cedar Grove; Uma P. Tripathi, Gladstone, all of N.J.

[73] Assignee: Playtex Products, Inc., Westport, Conn.

[21] Appl. No.: 457,250

[22] Filed: Jun. 1, 1995

[51] Int. Cl.$^6$ ..................... A61K 7/075

[52] U.S. Cl. .............. 424/401; 424/70.1; 424/70.12; 424/70.122; 424/70.28

[58] Field of Search ............... 424/401, 70.28, 424/70.1, 70.12, 70.122

[56] References Cited

U.S. PATENT DOCUMENTS

| | | | |
|---|---|---|---|
| 4,252,694 | 2/1981 | Lewis et al. | 252/545 |
| 4,337,166 | 6/1982 | Hill et al. | 252/174.15 |
| 4,364,837 | 12/1982 | Pader | 252/173 |
| 4,374,825 | 2/1983 | Bolich, Jr. et al. | 424/70 |
| 4,387,090 | 6/1983 | Bolich, Jr. et al. | 424/70 |
| 4,472,375 | 9/1984 | Bolich, Jr. et al. | 424/70 |
| 4,704,272 | 11/1987 | Oh et al. | 424/70 |
| 4,784,844 | 11/1988 | Thimineur et al. | 424/65 |
| 4,933,176 | 6/1990 | van Reeth | 424/70 |
| 5,185,325 | 2/1993 | Brawn | 514/23 |
| 5,246,703 | 9/1993 | Durfee | 424/70 |
| 5,372,806 | 12/1994 | Holloway | 424/70.1 |
| 5,409,628 | 4/1995 | Heinz et al. | 242/174.17 |
| 5,449,519 | 9/1995 | Wolf | 424/401 |

*Primary Examiner*—Thurman K. Page
*Assistant Examiner*—D. Faulkner
*Attorney, Agent, or Firm*—Ohlandt, Greeley, Ruggiero & Perle

[57] ABSTRACT

There is provided a hair care composition for protecting hair that is subjected to heat styling by a hair dryer or curling device. The composition comprises two compositions that naturally separate into distinct layers but easily intermix before use. The first composition prevents the hair from overdrying or heat dryout and, thus, leaving it brittle and more susceptible to cracking. The second composition prevents the hair from physical damage such as the rubbing and wear caused by brushing or combing. Thus, the present invention provides protection from heat dryout and physical damage that are commonly associated with heat styling.

49 Claims, No Drawings

DISCRETE HAIR CARE COMPOSITION

BACKGROUND OF THE INVENTION

I. Field of the Invention

The present invention relates generally to hair care compositions. More particularly, the present invention relates to hair care compositions for pre-treatment of hair before heating and styling. The compositions prevent damage to the pre-treated hair that is due to exposure to heat from a blow dryers, a curling device or the like, as well as to abrasive or frictional contact caused by a brush, a comb or the like.

Heat styling, such as the use of a blow dryer or curling device to heat the hair during styling, is prevalent amongst consumers. Unfortunately, heat styling can dry out and damage hair if the hair is subject to too much heat. For example, a person can overdry hair by holding a blow dryer too close to the hair or can overdry hair by holding a blow dryer or curling device too long at a particular spot of the hair. Moisture will be driven out of the hair so that the hair will become brittle and more susceptible to cracking. Such hair has heat dryout.

In addition, such heat styling can also cause physical damage to hair. For example, during such heat styling, the hair is brushed or combed. The constant rubbing and wear to the outer surface of the hair, leads to cracks and breaks in the hair. Moreover, dry hair, particularly dry hair suffering from heat dryout, is particularly susceptible to such physical damage.

II. Description of the Prior Art

Compositions, such as shampoos, conditioners, detergents and cosmetics, for cleaning, conditioning and/or moisturizing the hair are generally known. Such compositions are found in U.S. Pat. No. 4,364,837 to M. Pader, which issued on Dec. 21, 1982; U.S. Pat. No. 4,374,825 to R. E. Bolich, Jr., et al., which issued on Feb. 22, 1983; U.S. Pat. No. 4,387,090 to R. E. Bolich, Jr., which issued on Jun. 7, 1983; U.S. Pat. No. 4,472,375 to R.E. Bolich, Jr., et al., which issued on Sep. 18, 1984; U.S. Pat. No. 4,704,272 to Y. S. Oh, et al., which issued on Nov. 3, 1987; U.S. Pat. No. 4,784,844 to R. J. Thimineur, et al., which issued on Nov. 15, 1988; U.S. Pat. No. 4,933,176 to I. M. E. van Reeth, which issued on Jun. 12, 1990; U.S. Pat. No. 5,246,703 to L. D. Durfee, which issued on Sep. 21, 1993; U.S. Pat. No. 5,372,806 to T. L. Holloway, which issued Dec. 13, 1994; and U.S. Pat. No.5,409,628 to D. Heinz, et al, which issued on Apr. 25, 1995. See also, U.S. Pat. No. 4,252,694 to S. N. Lewis, et al., which issued on Feb. 24, 1981.

It is also known that consumer convenience is important in all hair care products. Accordingly, hair conditioning products may include a cyclic siloxane to improve their convenience for consumers. For example, U.S. Pat. No. 4,337,166 to M. P. L. Hill, et al., which issued on Jun. 29, 1982, provides a detergent composition for significantly reducing the drying time of hair after shampooing. The detergent composition includes one or more detergent substances and at least one cyclic siloxane.

None of the above patents, however, describes or suggests a hair care composition that has two phases. Furthermore, none of the above patents describe or suggest such a two phase hair care composition that also prevents the physical damage caused by brushing, combing or otherwise styling hair. In addition, none of the above patents describes or suggests a clear, transparent, two phase composition.

The present invention provides a hair care composition that protects the hair from both heat dryout, that normally occurs during heat styling, and physical damage. Also, the present invention provides an eye catching appearance that should be attractive to consumers. Thus, the present invention both overcomes the problems of the prior art and has an aesthetically pleasing appearance.

SUMMARY OF THE INVENTION

Against the foregoing background, it is a primary object of the present invention to provide a hair care composition that prevents physical damage caused by styling, such as brushing and combing, that typically accompanies the process of heat treating or styling hair with, for example, a blow dryer or curling device.

It is another object of the present invention to provide such a hair care composition having a first layer or composition for preventing physical damage cause by styling and another layer or composition for preventing heat dryout caused by heat styling.

It is a still another object of the present invention to provide such a hair care composition in which the two compositions may co-exist discretely, yet intermix when desired in the same container without degradation to the function or performance of either composition.

It is a further object of the present invention to provide such a hair care composition in which the two compositions naturally separate into two distinct, colored layers to provide an aesthetically pleasing and/or eye catching display to attract consumers.

It is a still further object of the present invention to provide such a hair care composition in which the two compositions are clear, transparent colored layers to provide an aesthetically pleasing and/or eye catching display to attract consumers.

To accomplish the foregoing objects and advantages, the present invention, in brief summary, is a hair care composition for treatment of hair before heat styling comprising: a discrete first composition having at least one moisture holding ingredient, an emulsifier and an ingredient that helps break the emulsion after use; and a discrete second composition having at least one lubricant. The first composition and the second composition are adapted to be combined to form the hair care composition prior to use to provide a single hair care composition that protects the hair from heat dryout and physical damage caused by heat styling.

The present invention further provides a hair care composition for treatment of hair before heat styling comprising: a first aqueous composition having at least one moisture holding ingredient, an emulsifier and an ingredient that helps break the emulsion after use; and a second non-aqueous composition having at least one lubricant, in which the first and second compositions provide protection from heat dryout and physical damage for heat styled hair in a single hair care composition, and in which the first composition is initially discrete from the second composition.

DETAILED DESCRIPTION OF THE PREFERRED EMBODIMENT

The present invention is a two phase or layer hair care composition that is applied to hair before heat styling. In particular, the hair care composition is applied before subjecting the hair to heat treatment or styling, such as blow drying or heat curling. Preferably, the hair care composition is applied to the hair after the use of cleaning compositions, such a shampoo and a conditioner, so that such cleaning compositions do not wash away the hair care composition.

It is also preferred that the hair care composition be applied before the application of general styling products to ensure direct contact to the hair.

The two phase hair care composition comprises a first aqueous composition phase or layer and a second non-aqueous composition phase or layer. Prior to application, these phases are mixed together as discussed below. In the most preferred embodiments, the two layers of the hair care composition should be clear, that is transparent.

In the preferred embodiments, the first aqueous composition is a water-based solution that includes at least one moisture holding ingredient that holds moisture in the hair. In addition, the first aqueous composition also includes an emulsifier and an ingredient that helps break the emulsion after use.

The moisture holding ingredient penetrates the hair and holds moisture in the hair. It has been found that heat styling, particularly blow drying, dries the moisture holding ingredient into the hair.

It is preferred that one moisture holding ingredient be a protein that also has some moisture holding properties. While any protein may be used, in the preferred embodiments of the present invention, the protein that has such moisture holding properties is hydrolyzed collagen. Hydrolyzed collagen is the hydrolysate of animal collagen derived by acid, enzyme or other method of hydrolysis. It is characterized by a significant level of hydroxyproline residues.

Another moisture holding ingredient is Panthenol. It is an alcohol having a formula $C_9H_{19}NO_4$. It is also known as dexpanthenol or 2,4-dihydroxy-N-(3-hydroxypropyl)-3,3-dimethylbutanamide. A third moisture holding ingredient is corn syrup. Corn syrup is an aqueous syrup prepared by acid and/or enzyme hydrolysis of corn starch and consists of varying mixtures of mono, di, and polysaccharides.

In the most preferred embodiment in which the hair care composition has two clear or transparent phases, hydrolyzed collagen, a protein/moisture holding ingredient, and panthenol and corn syrup, both moisture holding ingredients, are all present in the first aqueous composition. However, it has been found that in a preferred embodiment of the hair care composition may use only hydrolyzed collagen and panthenol as the moisture holding ingredients.

It is believed that the composition need not be completely transparent or completely clear, yet would still function. This could be achieved by substituting certain types of proteins for the hydrolyzed collagen. For example, such type proteins are quaternary proteins that perform well, except that the hair care composition will not be as transparent.

An emulsifier is included in the first aqueous solution to provide the layer separation characteristics described below. The preferred emulsifier is Glycereth-26. It has been found to reduce the oily feel of the non-aqueous composition. Glycereth-26 is a polyethylene glycol ether of glycerin having an average ethoxylation value of 26. In the preferred embodiments of the present hair care composition, Glycereth-26 is the primary emulsifier. It is desired to minimize the number and amount of emulsifiers, since emulsifiers leave an undesired residue on the hair.

The first aqueous composition needs an ingredient to help break the emulsion after use. Such an ingredient should be an electrolyte. In the preferred first aqueous composition, the electrolyte is sodium chloride.

In the preferred embodiments of the present hair care composition, the first aqueous composition includes an ingredient to aid in combing of the hair. This combing ingredient preferably is benzalkonium chloride. Benzalkonium chloride is a mixture of alkylbenzyldimethylammonium chlorides. As another benefit, the benzalkonium chloride acts as an emulsifier.

Also, preservatives, such as methylchloroisothiazolinone (5-Chloro-2-Methyl-4-Isothiazolin-3-one; and 4-Isothiazolin-3-one, 5-Chloro-2-Methyl-) and methylisothiazolinone (3(2H)-Isothiazolone, 2-Methyl-; 2-Methyl-3(2H)-Isothiazolone; and 2-Methyl-4-Isothiazolin-3-one), may be included in the first aqueous composition to provide further benefits to the preferred hair care composition. Such benefits include the prevention of microbial growth.

In the preferred embodiments of the present hair care composition, the first aqueous phase or composition has ingredients and their approximate range of percent composition by weight of the hair care composition as shown in Table A-1 below.

TABLE A-1

Aqueous Phase for Preferred Embodiment

| % by weight of Entire Composition | Ingredient | Type |
| --- | --- | --- |
| 65% to 79% | Water | |
| 0.10% to 0.30% | Hydrolyzed Collagen | protein/holds moisture |
| 0.10% to 0.30% | Panthenol | holds moisture |
| 0.20% to 0.50% | Corn Syrup | holds moisture |
| 0.10% to 0.20% | Benzalkonium Chloride | combing aid/emulsifier |
| 0.15% to 0.75% | Glycereth-26 | emulsifier |
| 0.40% to 0.80% | Sodium Chloride | helps break emulsion after use |
| up to 0.05% | Methylchloroisothiazolinone & Methylisothiazolinone | preservative |

The second non-aqueous phase or composition includes at least one lubricant to prevent physical damage to the hair due to styling. The lubricant is volatile and, thus, the heat applied to the hair during heat styling causes dissipation of the lubricant. Accordingly, the lubricant covers the hair during the brushing or combing to protect the hair, but then dissipates or is removed from the hair so that it does not leave a significant residue and does not weigh down the hair, as does conditioners and emulsifiers. However, a small amount of the lubricant may be left behind, and is desired, since such an amount provides the hair with shine.

While a single lubricant can be used in the second non-aqueous composition, in the preferred embodiments, the second non-aqueous composition includes two lubricants, one being a hydrocarbon and the other a silicone. A hydrocarbon is desired since coloring is desired in the second non-aqueous composition since it is perceived pleasing to consumers. Also, hydrocarbons reduce the oily feel of the silicone in the hair and provides the hair with a satin feel. Silicone is desired since it is a better lubricant than hydrocarbon. Accordingly, the preferred lubricants for the second non-aqueous composition include a hydrocarbon, such as isododecane or isohexadecane, and a silicone, such as cyclomethicone. The hydrocarbon and silicone are volatile ingredients so that they readily dissipate from the hair without residue and, thereby, without weighing down the hair.

Isododecane is a branched chain aliphatic hydrocarbon with 12 carbons. It is also known as heptane, 2,2,6,6-Tetramethyl-4-Methylene. Isohexadecane is a branched chain aliphatic hydrocarbon with 16 carbons, with a empirical formula $C_{16}H_{34}$. It is also known as 2,2,4,4,6,6,8 HeptamethylInonane; 2,2,4,4,6,8,8 HeptamethylInonane; Isohexadecane (EC Erdolchemie); Isohexadecane-Bayer (Bayer AG); Nonane, 2,2,4,4,6,8,8-Heptamethyl-Permethyl 101A (Presperse). Cyclomethicone is a cyclic dimethyl polysiloxane compound. It is described in detail in U.S. Pat. No. 4,337,166, which issued on Jun. 29, 1982, which patent has been described above and is incorporated herein by reference.

For the preferred embodiments, the second non-aqueous composition of the hair care composition includes the two lubricants with their approximate range of percent composition by weight as shown in Tables A-2(1) below.

TABLE A-2 (1)

Non-aqueous Phase For Preferred Embodiment

| % by weight of Entire Composition | Ingredient | Type |
|---|---|---|
| 12% to 22% | Isododecane | volatile hydrocarbon |
| 5% to 12% | Cyclomethicone | volatile silicone |

In an alternative embodiment in which isohexadecane is used as the volatile hydrocarbon instead of isododecane, the two lubricants with their approximate range of percent composition by weight as shown in Tables A-2(2) below.

TABLE A-2 (2)

Non-aqueous Phase For Preferred Embodiment

| % by weight of Entire Composition | Ingredient | Type |
|---|---|---|
| 5% to 15% | Isohexadecane | volatile hydrocarbon |
| 5% to 18% | Cyclomethicone | volatile silicone |

It is preferred that the first aqueous and the second non-aqueous compositions or phases each have a pleasing color, and that the entire hair care composition have an eye-catching appearance so that it stands out on the shelf. For the preferred embodiment, the two compositions are placed within a clear container, are transparent and appear as two distinct, discrete colored layers. The first aqueous or water composition is the bottom layer, while the second, non-aqueous composition is the top layer.

Color additives may be added to the first aqueous composition and the second non-aqueous composition to provide an aesthetically pleasing appearance for the hair care composition. The color additives are soluble in their respective composition but do not migrate into the other composition.

Also, fragrances may be added to the first aqueous solution and the second non-aqueous solution to provide a pleasing aroma. However, at present, a fragrance is present in only the second non-aqueous composition.

Thus, in the preferred compositions, the first aqueous composition and the second non-aqueous composition, recited in Tables A-1 and A-2(1) and (2), respectively, above, include a color additive and the second non-aqueous composition also includes a fragrance.

For dispensing, the two layers are mixed together by simply shaking the container. The two layers remain mixed for a particular length of time that is sufficient to dispense the hair care composition. When the container is left alone, the hair care composition will separate again into two distinct layers. For the preferred embodiment, the time required for the two compositions to begin to separate back into discrete layers is under a minute and, for normal shaking, about 20 to about 30 seconds.

EXAMPLE 1

Two most preferred formulas of the hair care composition are clear compositions and are derived based on the user's type of hair. The first formula is for dry, damaged hair and the second formula is for fine or thin hair. The differences in each formula are limited to slight differences in the percentage by weight of certain ingredients, as shown in Tables B-1, B-2(1)/(2), C-1 and C2(1)/(2) below, and the use of color in the first aqueous composition of the first formula. Tables B-1 and B-2(1)/(2) show the ingredients and their approximate percent composition by weight of the hair care composition for dry, damaged hair, and Tables C-1 and C-2(1)/(2) show ingredients and their approximate percent composition by weight of the hair care composition for fine or thin hair.

TABLE B-1

Aqueous Phase For First Formula
(Pink Color)

| % by weight of Entire Composition | Ingredient | Type |
|---|---|---|
| 77.97% | Water, Purified USP | |
| 0.25% | Hydrolyzed Collagen | protein/holds moisture |
| 0.25% | Panthenol | holds moisture |
| 0.40% | Corn Syrup | holds moisturizer |
| 0.13% | Benzalkonium Chloride | combing aid/emulsifier |
| 0.50% | Glycereth-26 | emulsifier |
| 0.50% | Sodium Chloride | helps break emulsion after use |
| 0.05% | Methylchloroisothiazolinone & Methylisothiazolinone | preservative |
| <0.01% | D&C Red No. 33 | color |

TABLE B-2 (1)

Non-aqueous Phase For First Formula
(Purple Color)

| % by weight of Entire Composition | Ingredient | Type |
|---|---|---|
| 13.29% | Isododecane | volatile hydrocarbon |
| 6.66% | Cyclomethicone | volatile silicone |
| 0.05% | Fragrance | |
| <0.01 | D&C Violet #2 | color |

In an alternative embodiment in which isohexadecane is used as the volatile hydrocarbon instead of isododecane, the non-aqueous phase with the approximate range of percent composition by weight of each ingredient is:

TABLE B-2 (2)

Non-aqueous Phase For First Formula
(Purple Color)

| % by weight of Entire Composition | Ingredient | Type |
|---|---|---|
| 5% to 15% | Isohexadecane | volatile hydrocarbon |
| 5% to 18% | Cyclomethicone | volatile silicone |
| 0.05% | Fragrance | |
| <0.01% | D&C Violet #2 | color |

TABLE C-1

Aqueous Phase For Second Formula (Colorless)

| % by weight of Entire Composition | Ingredient | Type |
|---|---|---|
| 78.57% | Water, Purified USP | |
| 0.15% | Hydrolyzed Collagen | protein/holds moisture |
| 0.15% | Panthenol | holds moisture |
| 0.20% | Corn Syrup | holds moisture |
| 0.13% | Benzalkonium Chloride | combing aid/emulsifier |
| 0.25% | Glycereth-26 | emulsifier |
| 0.50% | Sodium Chloride | helps break emulsion after use |
| 0.05% | Methylchloroisothia-zolinone & Methyl-isothiazolinone | preservative |

TABLE C-2 (1)

Non-aqueous Phase For Second Formula (Purple Color)

| % by weight of Entire Composition | Ingredient | Type |
|---|---|---|
| 13.29% | Isododecane | volatile hydrocarbon |
| 6.66% | Cyclomethicone | volatile silicone |
| 0.05% | Fragrance | |
| <0.01% | D&C Violet #2 | color |

In an alternative embodiment in which isohexadecane is used as the volatile hydrocarbon instead of isododecane, the non-aqueous phase with the approximate range of percent composition by weight of each ingredient is:

TABLE C-2 (2)

Non-aqueous Phase For Second Formula (Purple Color)

| % by weight of Entire Composition | Ingredient | Type |
|---|---|---|
| 5% to 15% | Isohexadecane | volatile hydrocarbon |
| 5% to 18% | Cyclomethicone | volatile silicone |
| 0.05% | Fragrance | |
| <0.01% | D&C Violet #2 | color |

As indicated above, in the most preferred embodiment, the first aqueous composition is about 80% by weight of the hair care composition and the second non-aqueous composition is about 20% by weight of the hair care composition.

In order to apply the hair care composition, the container for the hair care composition is shaken to mix the first aqueous composition with the second non-aqueous composition into a temporary emulsion. The mixture is then applied, such as by spraying, to delivering both parts to the hair. After application, the hair care composition may be distributed evenly throughout by, for example, brushing or combing the composition through the hair. Thereafter, the hair is heat styled as desired by the consumer.

EXAMPLE 2

An alternative type of hair care compositions having the ingredients and their approximate range of percent composition by weight shown in Tables D-1 and D-2 below may also be used. The alternative type shown below has a first aqueous composition of 70% by weight of the hair care composition and a second non-aqueous composition of 30% by weight of the hair care composition. One difference in this alternative type from the preferred types described in Example 1 is that significantly less water is used for the first aqueous composition of this alternative type. Even so, it has been determined through testing that the performance of all types of hair care compositions described in Examples 1 and 2 are about the same.

TABLE D-1

Aqueous Phase (Pink Color)

| % by weight of Entire Composition | Ingredient | Type |
|---|---|---|
| 67.92% | Water, Purified USP | |
| 0.25% | Hydrolyzed Collagen | protein/holds moisture |
| 0.25% | Panthenol | holds moisture |
| 0.40% | Corn Syrup | holds moisture |
| 0.13% | Benzalkonium Chloride | combing aid/emulsifier |
| 0.50% | Glycereth-26 | emulsifier |
| 0.50% | Sodium Chloride | helps break emulsion after use |
| 0.05% | Methylchloroisothia-zolinone & Methyl-isothiazolinone | preservative |
| <0.01% | D&C Red No. 33 | color |

TABLE D-2

Non-aqueous Phase (Purple Color)

| % by weight of Entire Composition | Ingredient | Type |
|---|---|---|
| 19.95% | Isododecane | volatile hydrocarbon |
| 10.00% | Cyclomethicone | volatile silicone |
| 0.05% | Fragrance | |
| <0.01% | D&C Violet #2 | color |

It is believed that the above two examples that show the ratio of the first aqueous composition to the second non-aqueous composition be 80% versus 20% (Example 1) and 70% versus 30% (Example 2) can vary even further, but perhaps without all the benefits of these embodiments. Nonetheless, it is believed that that the ratio of the first aqueous composition to the second non-aqueous composition can vary from 50/50 to 95/5, with the most preferred and preferred embodiments set forth above clearly falling within that range.

For example, when the ratio of the aqueous/nonaqueous compositions is 50/50 and 95/5 respectively, the % by weight of the hair care composition is as follows:

TABLE E-1

Aqueous Phase (Pink/Colorless)

| 50/50 ratio | 95/5 ratio | Ingredient/Type |
|---|---|---|
| 47.00 to 49.00 | 92.00 to 94.00 | Water, Purified USP |
| 0.10 to 0.30 | 0.10 to 0.30 | protein/holds moisture |
| 0.10 to 0.30 | 0.10 to 0.30 | Panthenol |
| 0.20 to 0.50 | 0.20 to 0.50 | Corn Syrup |
| 0.10 to 0.20 | 0.10 to 0.20 | Benzalkonium Chloride |
| 0.15 to 0.75 | 0.15 to 0.75 | Glycereth-26 |
| 0.40 to 0.80 | 0.40 to 0.80 | Sodium Chloride |

TABLE E-2

| Non-aqueous Phase (Purple Color) | | |
|---|---|---|
| 50/50 ratio | 95/5 ratio | Ingredient/Type |
| 5.00 to 50.00 | 1.00 to 5.00 | volatile hydrocarbon |
| 0.00 to 45.00 | 0.00 to 4.00 | volatile silicone |

It is understood that the first aqueous composition may include about 0.05% preservative, and <0.01% color, and that the second non-aqueous composition may include about 0.05% fragrance and <0.01% color.

As is shown in Table E-1 and E-2, the water and the lubricants vary while the remaining ingredients remain constant. Accordingly, for any ratio between 50/50 and 95/5, the water will proportionally increase as the lubricants proportionally decrease.

In addition, the amount of hydrocarbon, such as isododecane, may vary with respect to the amount of silicone, such as cyclomethicone even in the preferred embodiments, however Tables A through C set forth the most preferred ratio between the hydrocarbon and the silicone.

The invention having been thus described with particular reference to the preferred forms thereof, it will be obvious that various changes and modifications may be made therein without departing from the spirit and scope of the invention as defined in the appended claims.

Wherefore, we claim:

1. A hair care composition for treatment of hair before heat styling comprising:
   a discrete first layer comprising an aqueous composition, said aqueous composition having at least one moisture holding ingredient, an emulsifier and an ingredient that helps break emulsion after use; and
   a discrete second layer comprising a non-aqueous composition, said non-aqueous composition having at least one lubricant,
   wherein said first layer and said second layer remain discrete until said hair care composition is shaken, and wherein said aqueous composition and said non-aqueous composition form an emulsion upon shaking prior to use to provide a single hair care composition that protects the hair from heat dryout and physical damage caused by heat styling, and wherein said aqueous composition and said non-aqueous composition separate so that said first layer and said second layer are again discrete at a time after shaking is discontinued, and
   wherein said aqueous composition and said non-aqueous composition provide protection from heat dryout and physical damage for heat styled hair when mixed together as said emulsion.

2. The hair care composition of claim 1, wherein said at least one moisture holding ingredient is selected from the group consisting of: protein, panthenol and corn syrup.

3. The hair care composition of claim 2, wherein said protein is hydrolyzed collagen that makes the hair care composition completely transparent.

4. The hair care composition of claim 1, wherein said emulsifier is Glycereth-26.

5. The hair care composition of claim 1, wherein said ingredient to help break emulsion is sodium chloride.

6. The hair care composition of claim 1, further includes a combing aid.

7. The hair care composition of claim 6, wherein the combing aid is benzalkonium chloride.

8. The hair care composition of claim 1, wherein said lubricant is a volatile hydrocarbon.

9. The hair care composition of claim 8, wherein said volatile hydrocarbon is selected from a group consisting of isododecane and isohexadecane.

10. The hair care composition of claim 1, wherein said lubricant is a volatile silicone.

11. The hair care composition of claim 10, wherein said volatile silicone is a cyclomethicone.

12. A virtually transparent hair care composition for treatment of hair before heat styling comprising:
    a first aqueous layer comprising a first composition, said first composition having at least one moisture holding ingredient, an emulsifier and an ingredient that helps break emulsion after use; and
    a second non-aqueous layer comprising a second composition, said second composition having at least one lubricant,
    wherein said first aqueous layer is discrete from said second non-aqueous layer prior to being shaken, and wherein said first composition and said second composition form an emulsion upon shaking and subsequently separate at a time after said shaking is discontinued, and
    wherein said first composition and said second composition provide protection from heat dryout and physical damage for heat styled hair when mixed together as said emulsion to form the hair care composition.

13. A virtually transparent hair care composition for treatment of hair before heat styling comprising:
    a first layer comprising an aqueous composition, said aqueous composition having at least one moisture holding ingredient, an emulsifier and an ingredient that helps break emulsion after use, wherein said aqueous composition is about 50% to about 95% by weight of the hair care composition; and
    a second layer comprising a non-aqueous composition, said non-aqueous composition having at least one lubricant, wherein said non-aqueous composition is about 50% to about 5g by weight of the hair care composition,
    wherein said first layer is discrete from said second layer prior to being shaken, and wherein said aqueous composition and non-aqueous composition mix together upon shaking to form an emulsion, and subsequently separate at a time after shaking is discontinued, and,
    wherein said aqueous composition and said non-aqueous composition provide protection from heat dryout and physical damage for heat styled hair when mixed together as said emulsion to form the hair care composition.

14. The hair care composition of claim 13, wherein said first composition includes water in an amount about 47.00% to about 94.00% by weight of the hair care composition.

15. The hair care composition of claim 13, wherein said at least one moisture holding ingredient includes three moisture holding ingredients.

16. The hair care composition of claim 15, wherein said three moisture holding ingredients include a protein in an amount about 0.10% to about 0.30% by weight of the hair care composition, a panthenol that is about 0.10% to about 0.30% by weight of the hair care composition, and a corn syrup in an amount about 0.20% to about 0.50% by weight of the hair care composition.

17. The hair care composition of claim 16, wherein said emulsifier is Glycereth-26, and wherein said Glycereth-26 is about 0.15% to about 0.75% by weight of the hair care composition.

18. The hair care composition of claim 16, further comprising benzalkonium chloride in an amount about 0.10% to about 0.20% by weight of the hair care composition.

19. The hair care composition of claim 18, wherein said ingredient that helps break emulsion is sodium chloride, and wherein said sodium chloride is about 0.40% about 0.80% by weight of the hair care composition.

20. The hair care composition of claim 13, wherein said lubricant is a volatile hydrocarbon.

21. The hair care composition of claim 20, wherein said volatile hydrocarbon is about 1% to about 50% by weight of the hair care composition.

22. The hair care composition of claim 13, wherein said lubricant is a volatile silicone.

23. The hair care composition of claim 22, wherein said volatile silicone is up to about 45% by weight of the hair care composition.

24. The hair care composition of claim 13, wherein said first composition is about 70% to about 80% by weight of the hair care composition and said second composition is about 20% to about 30% by weight of the hair care composition.

25. The hair care composition of claim 1, wherein the ratio of said non-aqueous composition to said emulsifier is from about 6.6:1 to about 333:1.

26. The hair care composition of claim 12, wherein said first composition further includes water in an amount about 65% to about 80% by weight of the hair care composition.

27. The hair care composition of claim 12, wherein said at least one moisture holding ingredient includes at least one ingredient selected from the group consisting of: hydrolyzed collagen, panthenol and corn syrup.

28. The hair care composition of claim 12, wherein said at least one moisture holding ingredient includes hydrolyzed collagen and panthenol.

29. The hair care composition of claim 12, wherein said at least one moisture holding ingredient includes a hydrolyzed collagen that is about 0.10% to about 0.30% by weight of the hair care composition.

30. The hair care composition of claim 12, wherein said at least one moisture holding ingredient includes a panthenol that is about 0.10% to about 0.30% by weight of the hair care composition.

31. The hair care composition of claim 12, wherein said at least one moisture holding ingredient includes a corn syrup that is about 0.20% to about 0.50% by weight of the hair care composition.

32. The hair care composition of claim 12, wherein said emulsifier is Glycereth-26.

33. The hair care composition of claim 32, wherein said Glycereth-26 is about 0.15% to about 0.75% by weight of the hair care composition.

34. The hair care composition of claim 12, further comprising a combing aid.

35. The hair care composition of claim 34, wherein said combing aid is benzalkonium chloride.

36. The hair care composition of claim 35, wherein said benzalkonium chloride is about 0.10% to about 0.20% by weight of the hair care composition.

37. The hair care composition of claim 12, wherein said ingredient that helps break emulsion is sodium chloride.

38. The hair care composition of claim 37, wherein said sodium chloride is about 0.40% about 0.80% by weight of the hair care composition.

39. The hair care composition of claim 12, wherein said lubricant is a volatile hydrocarbon.

40. The hair care composition of claim 39, wherein said volatile hydrocarbon is about 5% to about 22% by weight of the hair care composition.

41. The hair care composition of claim 39, wherein said volatile hydrocarbon is selected from a group consisting of isododecane and isohexadecane.

42. The hair care composition of claim 12, wherein said lubricant is a volatile silicone.

43. The hair care composition of claim 42, wherein said volatile silicone is a cyclomethicone.

44. The hair care composition of claim 43, wherein said volatile silicone is about 5% to about 18% by weight of the hair care composition.

45. A transparent hair care composition for treatment of hair before heat styling comprising:

a first aqueous composition having water, hydrolyzed collagen, panthenol, corn syrup, benzalkonium chloride, Glycereth-26, and sodium chloride; and a second non-aqueous composition having isododecane and cyclomethicone, wherein said first composition is discrete from said second composition prior to being shaken, and wherein said first composition and said second composition mix together upon shaking and subsequently separate at a time after shaking is discontinued, and wherein said first composition and said second composition provide protection from heat dryout and physical damage for heat styled hair when mixed together in a single composition to form the hair care composition.

46. The hair care composition of claim 45, wherein the hair care composition is for use with dry, damaged hair, and wherein said first composition includes about 77.97% water, about 0.25% hydrolyzed collagen, about 0.25% panthenol, about 0.40% corn syrup, about 0.13% benzalkonium chloride, about 0.50% Glycereth-26, and about 0.50% sodium chloride, and wherein said second composition includes about 13.29% isododecane and about 6.66% cyclomethicone of the hair care composition.

47. The hair care composition of claim 12, wherein the ratio of said second composition to said emulsifier is from about 6.6:1 to about 333:1.

48. The hair care composition of claim 45, wherein the hair care composition is for use with fine hair, and wherein said first composition includes about 78.57% water, about 0.15% hydrolyzed collagen, about 0.15% panthenol, about 0.20% corn syrup, about 0.13% benzalkonium chloride, about 0.25% Glycereth-26, and about 0.50% sodium chloride, and wherein said second composition includes about 13.29% isododecane and about 6.66% cyclomethicone of the hair care composition.

49. The hair care composition of claim 45, wherein said first composition further includes about 0.05% preservative and <0.01% of color, and wherein said second composition further includes about 0.05% fragrance and <0.01% color of the hair care composition.

* * * * *

UNITED STATES PATENT AND TRADEMARK OFFICE
CERTIFICATE OF CORRECTION

PATENT NO. : 5,756,106

DATED : May 26, 1998

INVENTOR(S) : Linda M. Concannon, Joseph C. Hourihan and Uma P. Tripathi

It is certified that error appears in the above-identified patent and that said Letters Patent is hereby corrected as shown below:

On the title page, item [54], and col. 1, delete "DISCRETE".

Col. 9, line 36, delete "ingredient" and insert therefor --electrolyte--.
Col. 9, line 42, before "hair care composition" delete "said" and insert therefor --the--.
Col. 9, line 55, after "emulsion" insert --to form the hair care composition--.
Col. 9, line 65, delete "ingredient" and insert therefor --electrolyte--.
Col. 9, line 66, delete "includes" and insert therefor --including--.
Col. 10, line 16, delete "ingredient" and insert therefor --electrolyte--
Col. 10, line 25, before "shaking" delete "said".
Col. 10, line 35, delete "ingredient" and insert therefor --electrolyte--.
Col. 10, line 42, delete "5g" and insert therefor --5%--.
Col. 11, line 9, delete "ingredient" and insert therefor --electrolyte--.
Col. 11, line 10, after "0.40%" insert --to--.
Col. 11, line 65, delete "ingredient" and insert therefor --electrolyte--.

UNITED STATES PATENT AND TRADEMARK OFFICE
CERTIFICATE OF CORRECTION

PATENT NO. : 5,756,106
DATED : May 26, 1998
INVENTOR(S) : Linda M. Concannon, et al.

It is certified that error appears in the above-identified patent and that said Letters Patent is hereby corrected as shown below:

Col. 12, line 2, after "0.40%" insert --to--.
Col. 12, line 10, before "group" delete "a" and insert therefor --the--.

Signed and Sealed this

Twenty-sixth Day of January, 1999

Attest:

Attesting Officer

Acting Commissioner of Patents and Trademarks